United States Patent [19]

Skillern

[11] 4,443,442

[45] Apr. 17, 1984

[54] METHOD AND COMPOSITION FOR TREATMENT OF ACNE VULGARIS

[76] Inventor: Scott D. Skillern, 722 E. Colfax St., South Bend, Ind. 46617

[21] Appl. No.: 106,224

[22] Filed: Dec. 21, 1979

[51] Int. Cl.³ ............................................. A61K 31/54
[52] U.S. Cl. ................................................... 424/246
[58] Field of Search ............... 424/227, 246, 153, 301, 424/313

[56] References Cited

U.S. PATENT DOCUMENTS 4,005,198  1/1977  Skillern et al. ...................... 424/227

OTHER PUBLICATIONS

Frank, "Acne Vulgaris", Charles C. Thomas, Publ., 1976, pp. 329-340.
Gordon et al., Med. J. Aust., 1971, 2:565-570.
Physicians Desk Reference-26th Ed., 1972, pp. 506-508.
Cutting's Handbook of Pharmacology, 4th Ed., 1969, pp. 234-237.

Primary Examiner—Leonard Schenkman

[57] ABSTRACT

This invention relates to an improved method and composition for controlling all grades of *acne vulgaris* using a combination of sodium in the form of a pharmacologically acceptable sodium salt and an acne controlling compound selected from the group consisting of methyclothiazide, polythiazide and trichlormethazide, which is therapeutically effective in increasing sodium excretion in the sebaceous gland thereby controlling *acne vulgaris* eruptions. The conjoint use of the sodium salt and the acne controlling compound significantly reduces the unwanted side effects caused by the administration of the acne controlling compound including nausea, dizziness, hypotension and diuresis, which are experienced in some patients when the acne controlling compound is employed in acne treatment absent the conjoint use of the sodium salt.

In a preferred embodiment the acne controlling compound and the sodium salt are employed in an acne treatment therapy which includes the use of a therapeutic *acne vulgaris* affecting amount of an antibiotic effective against *acne vulgaris*.

5 Claims, No Drawings

METHOD AND COMPOSITION FOR TREATMENT OF ACNE VULGARIS

BACKGROUND OF THE INVENTION

A method for the treatment of acne vulgaris as disclosed in U.S. Pat. No. 4,005,198, by the inventor herein which is herein incorporated by reference, is the bi-daily oral administration of methyclothiazide, optionally with the daily concurrent administration of tetracycline. However, it has been observed that the oral ingestion of a therapeutically effective dosage of methylclothiazide or particularly other compounds such as polythiazide and trichlormethazide creates at least one of the unwanted side effects of diuresis, dizziness, nausea and clinical orthostatic hypotension in some patients.

DESCRIPTION OF THE INVENTION

This invention relates to an improved method and composition for controlling all grades of acne vulgaris using a combination of sodium in the form of a pharmacologically acceptable sodium salt and an acne controlling compound selected from the group consisting of methyclothiazide, polythiazide and trichlormethazide, which is therapeutically effective in increasing sodium excretion in the sebaceous gland thereby controlling acne vulgaris eruptions. The conjoint use of the sodium salt and the acne controlling compound significantly reduces the unwanted side effects caused by the administration of the acne controlling compound including nausea, dizziness, hypotension and diuresis, which are experienced in some patients when the acne controlling compound is employed in acne treatment absent the conjoint of the sodium salt.

In a preferred embodiment the acne controlling compound and the sodium salt are employed in an acne treatment therapy which includes the use of a therapeutic acne vulgaris affecting amount of an antibiotic effective against acne vulgaris.

The sodium salts which can be conjointly used in the present invention include any pharmacologically (physiologically) acceptable sodium salt which is capable of increasing serum sodium levels in the body. Sodium chloride is the preferred salt which is useful in the present invention, however, illustrative examples of other sodium salts which are useful in counteracting the unwanted side effects of the acne controlling compounds include, but are not limited to: sodium bicarbonate, sodium carbonate and sodium citrate.

The acne controlling compounds which are useful in the present invention include methyclothiazide (6-chloro-7-sulfanoyl-3,4-dihydro-2-methyl-2,2,4-benzothiadiazine-1,1-dioxide; Enduron), polythiazide (2-methyl-3,4-dihdyro-3-2',2',2'-trifluoro-ethylthiomethyl)-6-chloro-7-sulfamyl-1,2,4-benzothiadiazine-1,1-dioxide; Renese), and trichlormethazide (3-dichloromethyl-6-chloro-7-sulfanyl 3,4-dihydro-1,2,4-benzothiadiazide-1,1-dioxide; Naqua).

The preferred acne controlling compound for use in the present invention is methyclothiazide.

It is noted that several apparently structurally related compounds such as chlorothiazide, which are employed in diuretic therapy, have little or no effect in controlling acne vulgaris and/or continue to display side effects including dizziness, nausea, diuresis or hypotension when conjointly administered with a sodium salt.

The antibiotics which can be conjointly administered with the sodium salt and the acne controlling compound include any antibiotic which effectively inhibits acne causing bacterium, for example, *Propiona bacterium acne*. Illustrative examples of antibiotics which can be employed in the present invention include but are not limited to: tetracycline and its derivatives, erythromycin and its derivatives, minomycin, cleosin, orthomycin, clindamycin and topocycline.

Typically, the amount of sodium salt employed in the present invention is an amount at least sufficient to reduce the incidence of diuresis, dizziness, nausea and clinical hypotension which can be caused by the ingestion of the acne controlling compounds. A patient need only minimally ingest 0.2 grams of sodium as is approximately contained in 0.5 grams of sodium chloride. While an upper limit to the amount of sodium salt which can be ingested depends on individual patient tolerance, a reasonable maximum amount of sodium salt is about 0.8 grams of sodium as is approximately contained in 2.0 grams of sodium chloride. The preferred amount of salt per dose of acne controlling compound is 0.25 to 0.4 grams of sodium as is approximately contained in 0.7 to 1.0 grams of sodium chloride.

The required dosage of the acne controlling compound which is useful in the present invention must be of a sufficient amount to trigger sodium excretion in the sebaceous glands. Dosages of the acne controlling compounds which are useful in the present invention range from 1.0 to 10.0 mg. Dosages are preferably prescribed for patients in correlation with their weight. An effective acne treatment may be performed on some patients with as little as approximately 0.01 mg. of acne controlling compound per lb. weight of patient or as high as 0.07 mg. of acne controlling compound per lb. weight of patient. The preferred dosage range for administering methylclothiazide is from 2.0 to 8.0 mg. per patient.

A typical dosage schedule for administering methyclothiazide for an effective acne treatment is 1.2 to 5.0 mg. for humans up to 120 pounds, 4.0 to 7.5 mg. for humans weighing between 121 to 156 pounds, and 5.0 to 10.0 mg. for humans weighing more than 156 pounds.

The dosage range of polythiazine and trichlormethazide which have been found to be effective in combatting acne are approximately one-half the dosage range of methyclothiazide, that is, 0.5 to 5.0 mg., preferably 1.0 to 4.0 mg. per patient.

It is preferred that methyclothiazide, polythiazide or trichlormethazide not be administered in dosages greater than the dosage range mentioned above as it becomes extremely difficult to overcome the diuretic and hypotensive side effects of these compounds with the conjoint administration of sodium salt.

It was found that the conjoint administration of methyclothiazide and a sodium salt produced the most effective treatment of acne vulgaris and the most effective elimination of any side effects such as diuresis, dizziness, nausea, or hypotension. While a sodium salt reduces the side effects of either polythiazide or trichlormethazide, a higher incidence of diuresis is still experienced in these cases.

It has been found that methyclothiazide, polythiazide and trichlormethazide are most effective for their use in acne control (elimination or moderation) when they are administered conjointly with a sodium salt every other day, that is, on a bi-daily basis. This mode of administration provides the smallest incidence of side effects. At least with methyclothiazide, bi-daily administration of the acne controlling compound retards the individual buildup of the acne controlling compound in the body of the patient as the body does not metabolize methyclothiazide, and excretes it unchanged, usually within a 24 hour period after ingestion.

While it is suggested that the acne controlling compound be administered bi-daily, the daily administration or the administration every third or fourth day of the acne controlling compound is included within the scope of the present invention. Regardless of whether the acne controlling compound is administered daily, bi-daily or otherwise, the dosage remains the same as discussed above.

While the combination of a sodium salt with either methyclothiazide, polythiazide or trichlorthiazide in the above-discussed dosages is effective in combatting acne, a patient can also employ daily or bi-daily therapeutically effective amounts of antibiotics and other pharmacological agents which are effective in inhibiting acne causing baterium such as *Propiona bacterium acne*. These antibiotics can be administered orally, topically or subcutaneously in an amount and by a mode known per se in the art. Examples of antibiotics and pharmacological agents which can be usefully co-employed with the conjoint administration of a sodum salt and a acne controlling compound include but are not limited to: erythromycin and its derivatives, tetracycline and its derivatives, minocycline, cleosin, orthomycin, clindamycin, topocycline, sulfa drugs, tretinoin, salicylic acid, benzoyl peroxide and hydrogen peroxide.

While antibiotics such as erythromycin and tetracycline are generally prescribed for cases of acne vulgaris in oral dosages of 500 to 1,000 mg. per day, these dosages or subminimal dosages of these antibiotics can be used along with the conjoint use of sodium salt and the acne controlling compound. Any therapeutically effective amount of an acne combatting oral antibiotic can be incorporated into the salt acne controlling compound combination or can be taken separately.

Erythromycin, tetracycline and tetracycline hydrochloride, chlorotetracycline, oxytetracyclone, onegamycin or any other antibacterial drug can be taken in daily dosages of approximately 150 mg. to 2 grams, preferrably 150 mg. to 500 mg., and most preferrably 250 mg. The combined use of one of these antibiotics with the previously mentioned dosages of a sodium salt and the acne controlling compounds form a basis of treatment which results in superior acne control of all grades of acne vulgaris particularly grades 1/10th through 5. It is preferred that the oral antibiotic be taken on a daily basis so that the body receives a daily dosage of the oral antibiotic.

The sodium salt and the acne controlling compound can be orally taken either individually or in a single combined dosage unit for example, a tablet or a capsule. An antibiotic can be taken by the patient either as a separate entity or in combination with the sodium salt, the acne controlling substance or both of these compounds. It is preferred that the salt and the acne controlling compound be taken as a single entity such as in one capsule or pill. This procedure minimizes the error associated with the physician to patient explanation. By combining these ingredients into one dosage, the patient compliance factor increases as an extra patient performance step is eliminated.

Methyclothiazide, polythiazide and trichlormethazide are well known drugs having diuretic and saluretic effects which result from drug induced inhibition of the renal tubular reabsorption of electrolytes. The ingestion of any of these acne controlling compounds greatly enhance the excretion of sodium and chloride in both the renal and sebaceous glands while potassium excretion is lowered.

Maximum adult dosages of diuretics such as methyclothiazide usually range from 2.5 to 10 mg. daily when administered for diuretic effects. However, diuretic effects are one of its unwanted side effects with respect to its functional use in acne care in the present invention.

There is significant natruresis and diuresis within two hours after the administration of a single dose of a methyclothiazide, polythiazide or trichlormethazide. These effects peak within about six hours and persist for about 24 hours. Methyclothiazide, polythiazide and trichlormethazide have antihypertensive properties which produce a reduction in blood pressure. Since the acne controlling compounds are herein employed for their acne controlling function in what is presupposed to be a patient having normal blood pressure, the antihypertensive function of these compounds is an undesired effect.

Since methyclothiazide, polythiazide or trichlormethiazide are ingested in the present invention for acne care only and not for their diuretic or antihypertensive activity, the conjoint administration of a sodium salt with one of these compounds presents a situation where a drug having multiple effects can be regulated to obtain the sole effect of a drug which is desired.

It is believed that the acne controlling compounds function as acne controlling agents by the following mechanism. These compounds act on the renal tubules with the effect of excreting sodium and chloride. This excretion process occurs to a much lesser extent in the sebaceous glands. It is believed that the excess sodium migrates through the sebaceous gland and follicle and chemically combines with free fatty acids present therein to form the salt of the fatty acids which unlike free fatty acids do not support growth of acne bacterial flora.

It is well known in the art that certain diuretics are more potent than others, that is, different diuretics produce varying degrees of sodium and chloride excretion in the body. It appears that while all compounds useful as diuretics produce excretions in the renal tubules, only methyclothiazide, polythiazide and trichlormethazide are reasonably useful in the treatment of acne vulgaris in otherwise normal patients.

The present concept accepted by most doctors in the dermatological field is that oral antibiotics such as tetracycline act in such a way as to lessen the flow of the free fatty acid from the sebaceous gland. This action helps to improve the acne by limiting the amount of free fatty acids which can be decomposed in clinical acne within the sebaceous gland and follicle. Any amount of antibiotic which reduces the amount of free fatty acid in the follicle is at least a minimally effective amount against acne.

The following are typical treatment for a patient having acne vulgaris in the severity of Grade 1/10th through Grade 5. The dosage of acne controlling compound is preferrably prescribed in accordance with the patient weight schedule.

A 90 lb. patient takes one capsule of oral tetracycline 250 mg. USP or Erythromycin 250 mg. USP daily. The patient is told to orally ingest one methyclothiazide-sodium chloride dose unit every other day containing 1.0 grams of sodium chloride and 2.5 mg. of methyclothiazide. Alternatively, the patient can ingest one 2.5 mg. methyclothiazide tablet and a 1.0 gm. sodium chloride tablet.

A 135 lb. patient is told to ingest one methyclothizidesodium chloride dose unit containing 1.0 grams of sodium chloride and 5.0 mg. of methyclothiazide on a bi-daily basis. The patient is additionally told to take one capsule of oral tetracycline 250 mg. USP daily.

A 170 lb. patient is told to ingest one methyclothiazidesodium chloride dose unit containing 1.0 grams of sodium chloride and 7.5 mg. of methyclothiazide on a bi-daily basis. The patient is additionally told to take one capsule of oral tetracycline 250 mg. USP daily.

In this treatment of acne vulgaris it is preferred that the patient ingest the acne controlling compound and the sodium salt in conjunction with the intake of water or an aqueous fluid. Typically, in addition to water accumulated through eating, it is preferred that the patient drink approximately 10 ounces of fluid bi-daily with the acne controlling compound.

The patient is cautioned to absolutely avoid eating any chocolate and in some instances it may be necessary to further reduce the patient's iodine intake for better acne control by restricting their intake of high iodine foods. For this reason, it is preferred to employ non-iodized sodium chloride in the present invention as many commercially available table salts contain iodine.

Some patients are further instructed to apply a topical acne gel of a benzoyl peroxide derivative to the active acne lesions each night at bedtime. The necessity for this procedure rapidly diminishes after one to two months.

The patient is advised that no improvement of the acne will be noticeable for the first ten days, but thereafter, they should expect to see a steady improvement to the point that 85% to 100% of the acne is cleared up in two to seven months.

There follow a number of examples which typify the conjoint use of the sodium salt and the acne controlling compounds in the present example.

EXAMPLE 1

Thirty patients under treatment for acne care were administered a dosage of methyclothiazide in accordance with the dosage-patient weight schedule. Additionally, thirty patients were conjointly administered a dosage of methyclothiazide and one gram of sodium chloride. The blood pressure of the patients was recorded prior to the ingestion of the methyclothiazide and/or sodium chloride and again at a time period of approximately nine hours after the ingestion of the methyclothiazide and/or sodium chloride. The results of the individual tests are shown in Table I. The results of the individual tests in Table I are averaged in Table IA.

The results in Table I and IA demonstrate that the conjoint use of methyclothiazide and a sodium salt in comparison to the sole use of methyclothiazide reduces the degree of diastolic reduction occuring nine hours after the patient has ingested methyclothiazide.

Similarly, the results of the tests tabulated in Tables I and IA demonstrate that the conjoint use of methyclothiazide and sodium chloride totally eliminate any complaints of diuresis such as those which occurred when methyclothiazide was administered without the sodium salt.

EXAMPLE 2

Tests were conducted as in the procedure of Example 1 except trichlormethiazide was administered instead of methyclothiazide to a total of forty patients. Twenty patients were conjointly administered sodium chloride with the trichlormethiazide while twenty patients were administered a dose of trichlormethiazide and no salt. The dosages of sodium chloride and trichlormethiazide as well as the results of this test are displayed in Table II and the results are averaged in Table IIA.

As demonstrated in Tables II and IIA the average diastolic reduction was greater for patients in the same weight class who did not conjointly use sodium chloride with the dosage of trichloromethiazide. Thus the conjoint administration of sodium chloride with trichlormethiazide created an overall reduction in the degree of average diastolic reduction in the patients as opposed to the sole administration of trichlormethiazide.

The results of Tables II and IIA further demonstrate a slight reduction in the degree of the complaints of diuresis when a patient was conjointly administered sodium chloride and trichlormethiazide as opposed to the sole administration of trichlormethiazide.

EXAMPLE 3

Tests were conducted as in the procedure of Example 1 except polythiazide was administered instead of methyclothiazide. The patients were conjointly administered sodium chloride with the polythiazide while ten patients were administered a dose of polythiazide and no sodium chloride. The disages of sodium chloride and polythiazide as well as the results of this test are displayed in Table III and are averaged in Table IIIA.

As demonstrated in Tables III and IIIA, the average diastolic reduction was significantly reduced for patients who were conjointly administered sodium chloride and polythiazide as opposed to those patients who were solely administered polythiazide.

The results in Table III further demonstrate a slight reduction in the degree of the complaints of diuresis when the polythiazide is administered at a dosage of two mgs. However, at an increased dosage of four mgs. of polythiazide the conjoint administration of one gram of sodium chloride did not reduce the complaints of diuresis.

TABLE I

| Dosage | | | Blood Pressure of Patient | | | |
|---|---|---|---|---|---|---|
| Methclothiazide (mg.) | NaCl (gram) | Weight of Patient | Before Ingestion | 9 hours after ingestion of methyclothiazide | Diastolic Reduction | Complaints of Diuresis |
| 2.5 | 0 | 107 | 114/82 | 118/74 | −8 | Moderate |
| 2.5 | 0 | 105 | 118/78 | 116/72 | −6 | — |
| 2.5 | 0 | 116 | 108/72 | 106/66 | −8 | Mild |
| 2.5 | 0 | 118 | 112/76 | 110/70 | −6 | — |
| 2.5 | 0 | 100 | 104/64 | 90/60 | −4 | — |
| 2.5 | 0 | 115 | 108/76 | 100/69 | −7 | — |

TABLE I-continued

| Dosage | | | Blood Pressure of Patient | | | |
|---|---|---|---|---|---|---|
| Methclothiazide (mg.) | NaCl (gram) | Weight of Patient | Before Ingestion | 9 hours after ingestion of methyclothiazide | Diastolic Reduction | Complaints of Diuresis |
| 2.5 | 0 | 108 | 98/62 | 90/60 | −2 | — |
| 2.5 | 0 | 90 | 92/64 | 90/60 | −4 | — |
| 2.5 | 0 | 108 | 118/70 | 110/64 | −6 | Moderate |
| 2.5 | 0 | 118 | 98/66 | 90/60 | −6 | Moderate |
| 5.0 | 0 | 140 | 114/74 | 108/62 | −12 | Mild |
| 5.0 | 0 | 123 | 118/68 | 100/60 | −8 | — |
| 5.0 | 0 | 130 | 110/72 | 107/65 | −7 | — |
| 5.0 | 0 | 121 | 110/70 | 120/62 | −8 | — |
| 5.0 | 0 | 134 | 112/82 | 110/73 | −9 | Mild |
| 5.0 | 0 | 143 | 118/68 | 112/61 | −7 | — |
| 5.0 | 0 | 123 | 102/64 | 90/60 | −4 | — |
| 5.0 | 0 | 133 | 108/76 | 102/66 | −10 | Moderate |
| 5.0 | 0 | 125 | 128/70 | 92/60 | −10 | — |
| 5.0 | 0 | 145 | 118/62 | 100/60 | −2 | — |
| 7.5 | 0 | 160 | 108/60 | 90/60 | −0 | — |
| 7.5 | 0 | 156 | 104/76 | 100/66 | −10 | — |
| 7.5 | 0 | 165 | 114/68 | 114/70 | +2 | — |
| 7.5 | 0 | 176 | 130/80 | 124/70 | −10 | — |
| 7.5 | 0 | 158 | 124/72 | 124/66 | −6 | — |
| 7.5 | 0 | 180 | 126/72 | 123/66 | −6 | — |
| 7.5 | 0 | 158 | 106/72 | 104/66 | −6 | — |
| 7.5 | 0 | 160 | 102/72 | 100/68 | −4 | — |
| 7.5 | 0 | 160 | 106/70 | 110/66 | −4 | — |
| 7.5 | 0 | 168 | 134/82 | 126/72 | −10 | — |
| 2.5 | 1.0 | 107 | 118/84 | 120/80 | −4 | — |
| 2.5 | 1.0 | 105 | 118/76 | 118/72 | −4 | — |
| 2.5 | 1.0 | 116 | 110/70 | 108/68 | −4 | — |
| 2.5 | 1.0 | 108 | 98/62 | 90/60 | −2 | — |
| 2.5 | 1.0 | 90 | 92/60 | 90/60 | 0 | — |
| 2.5 | 1.0 | 118 | 118/74 | 114/70 | −4 | — |
| 2.5 | 1.0 | 100 | 90/60 | 90/60 | 0 | — |
| 2.5 | 1.0 | 116 | 110/70 | 108/66 | −4 | — |
| 2.5 | 1.0 | 118 | 112/68 | 110/66 | −2 | — |
| 2.5 | 1.0 | 107 | 100/60 | 92/60 | 0 | — |
| 5.0 | 1.0 | 140 | 116/72 | 112/66 | −6 | — |
| 5.0 | 1.0 | 123 | 120/70 | 110/66 | −4 | — |
| 5.0 | 1.0 | 130 | 110/70 | 110/68 | −2 | — |
| 5.0 | 1.0 | 121 | 110/70 | 106/64 | −6 | — |
| 5.0 | 1.0 | 143 | 112/70 | 106/64 | −6 | — |
| 5.0 | 1.0 | 123 | 106/70 | 96/66 | −4 | — |
| 5.0 | 1.0 | 152 | 96/66 | 96/66 | 0 | — |
| 5.0 | 1.0 | 138 | 105/95 | 110/60 | −5 | — |
| 5.0 | 1.0 | 128 | 124/78 | 120/70 | −8 | — |
| 5.0 | 1.0 | 150 | 118/70 | 110/66 | −4 | — |
| 7.5 | 1.0 | 176 | 118/64 | 120/70 | +6 | — |
| 7.5 | 1.0 | 158 | 124/72 | 126/68 | −4 | — |
| 7.5 | 1.0 | 180 | 120/70 | 120/70 | 0 | — |
| 7.5 | 1.0 | 156 | 104/76 | 100/70 | −6 | — |
| 7.5 | 1.0 | 163 | 130/80 | 130/76 | −4 | — |
| 7.5 | 1.0 | 163 | 98/60 | 100/60 | 0 | — |
| 7.5 | 1.0 | 180 | 122/68 | 126/74 | +6 | — |
| 7.5 | 1.0 | 160 | 108/70 | 110/70 | 0 | — |

TABLE 1A

| Dosage | | | Weight | Average Blood Pressure of Patients | | | Complaints of Diuresis | | |
|---|---|---|---|---|---|---|---|---|---|
| Methyl-clothiazide (mg.) | NaCl (gr.) | No. of Patients Tested | Range of Patient (lbs.) | Before Ingestion | 9 Hours After Ingestion of Methyl-clothiazide | Average Diastolic Reduction | Mild | Moderate | Servere |
| 2.5 | 0 | 10 | under 120 | 107/71 | 102/65.5 | −5.5 | 1 | 3 | 0 |
| 5.0 | 0 | 10 | 120–155 | 112.8/70.6 | 104/1/62.2 | −8.4 | 2 | 1 | 0 |
| 7.5 | 0 | 10 | over 155 | 113.4/72.4 | 111.5/67.0 | −5.4 | 0 | 0 | 0 |
| 2.5 | 1.0 | 10 | under 120 | 107.6/68.4 | 103.4/66.2 | −2.2 | 0 | 0 | 0 |
| 5.0 | 1.0 | 10 | 120–155 | 112.7/70.1 | 107.6/65.8 | −4.3 | 0 | 0 | 0 |
| 7.5 | 1.0 | 10 | over 155 | 116.4/70 | 117.2/69.8 | −0.2 | 0 | 0 | 0 |

TABLE II

| Dosage Trichlormethiazide (mg.) | NaCl (gram) | Weight of Patient | Blood Pressure of Patient Before Ingestion | 9 hours after ingestion of Trichlormethiazide | Diastolic Reduction | Complaints of Diuresis (if blank-none) |
|---|---|---|---|---|---|---|
| 2.0 | 0 | 108 | 100/64 | 90/60 | −4 | mild |
| 2.0 | 0 | 107 | 120/78 | 114/70 | −6 | — |
| 2.0 | 0 | 109 | 98/62 | 90/60 | −2 | — |
| 2.0 | 0 | 118 | 120/70 | 110/60 | −10 | moderate |
| 2.0 | 0 | 115 | 116/70 | 100/62 | −8 | — |
| 2.0 | 0 | 110 | 122/82 | 110/72 | −10 | — |
| 2.0 | 0 | 116 | 86/54 | 90/50 | −4 | — |
| 2.0 | 0 | 119 | 118/86 | 110/74 | −12 | mild |
| 2.0 | 0 | 112 | 118/70 | 108/62 | −8 | — |
| 2.0 | 0 | 110 | 104/68 | 90/60 | −8 | mild |
| 4.0 | 0 | 140 | 118/70 | 92/58 | −12 | moderate |
| 4.0 | 0 | 123 | 110/70 | 100/60 | −10 | moderate |
| 4.0 | 0 | 128 | 112/70 | 104/66 | −12 | mild |
| 4.0 | 0 | 143 | 110/72 | 100/60 | −12 | — |
| 4.0 | 0 | 134 | 118/80 | 100/70 | −10 | — |
| 4.0 | 0 | 146 | 130/62 | 124/56 | −6 | — |
| 4.0 | 0 | 145 | 120/80 | 110/68 | −12 | mild |
| 4.0 | 0 | 150 | 106/68 | 100/62 | −6 | moderate |
| 4.0 | 0 | 124 | 112/76 | 110/62 | −14 | — |
| 4.0 | 0 | 133 | 102/72 | 100/66 | −6 | — |
| 2.0 | 1.0 | 108 | 108/68 | 100/60 | −8 | moderate |
| 2.0 | 1.0 | 107 | 120/80 | 110/74 | −6 | mild |
| 2.0 | 1.0 | 119 | 120/80 | 116/74 | −6 | — |
| 2.0 | 1.0 | 109 | 100/64 | 90/60 | −4 | — |
| 2.0 | 1.0 | 112 | 120/74 | 110/70 | −4 | — |
| 2.0 | 1.0 | 110 | 110/70 | 110/64 | −6 | — |
| 2.0 | 1.0 | 116 | 96/62 | 90/60 | −2 | — |
| 2.0 | 1.0 | 119 | 122/78 | 120/70 | −8 | mild |
| 2.0 | 1.0 | 120 | 118/82 | 116/76 | −6 | — |
| 2.0 | 1.0 | 120 | 110/70 | 120/66 | −4 | mild |
| 4.0 | 1.0 | 140 | 120/76 | 100/68 | −8 | mild |
| 4.0 | 1.0 | 123 | 110/70 | 106/64 | −6 | — |
| 4.0 | 1.0 | 128 | 120/80 | 122/72 | −8 | moderate |
| 4.0 | 1.0 | 150 | 120/84 | 120/76 | −8 | — |
| 4.0 | 1.0 | 146 | 130/70 | 130/66 | −4 | — |
| 4.0 | 1.0 | 134 | 116/76 | 120/70 | −6 | — |
| 4.0 | 1.0 | 138 | 98/68 | 104/62 | −6 | — |
| 4.0 | 1.0 | 153 | 130/80 | 128/70 | −10 | mild |
| 4.0 | 1.0 | 126 | 102/68 | 110/60 | −8 | mild |
| 4.0 | 1.0 | 145 | 116/82 | 110/72 | −10 | mild |

TABLE IIA

| No. of Patients Tested | Dosage Trichlormethiazide (mg) | NaCl (gm) | Weight Range of Patients | Average Blood Pressure of Patients Normal | 9 hours after ingesting trichlormethiazide | Average Diastolic Reduction | Complaints of Diuresis Mild | Moderate | Severe |
|---|---|---|---|---|---|---|---|---|---|
| 10 | 2 | 0 | 107–119 | 110.4/70.4 | 102.2/63 | −7.4 | 3 | 1 | 0 |
| 10 | 4 | 0 | 123–150 | 113.8/72 | 105/62.8 | −9.2 | 2 | 3 | 0 |
| 10 | 2 | 1.0 | 107–120 | 112.4/72.8 | 108.2/67.4 | −5.4 | 3 | 1 | 0 |
| 10 | 4 | 1.0 | 123–153 | 116.2/75.4 | 115/68.0 | −7.4 | 4 | 1 | 0 |

TABLE III

| Dosage Polythiazide (mg.) | NaCl (gr.) | Weight of Patient | Blood Pressure of Patient Before Ingestion | 9 hours after ingestion of polythiazide | Diastolic Reduction | Complaints of Diuresis |
|---|---|---|---|---|---|---|
| 2.0 | 0 | 138 | 118/70 | 114/60 | −10 | moderate |
| 2.0 | 0 | 168 | 120/80 | 110/70 | −10 | mild |
| 2.0 | 0 | 135 | 105/60 | 90/60 | 0 | moderate |
| 2.0 | 0 | 150 | 110/80 | 100/70 | −10 | moderate |
| 2.0 | 0 | 148 | 114/60 | 100/60 | 0 | moderate |
| 4.0 | 0 | 138 | 124/68 | 110/60 | −8 | mild |
| 4.0 | 0 | 168 | 120/80 | 110/60 | −20 | mild |
| 4.0 | 0 | 135 | 108/60 | 90/60 | 0 | — |
| 4.0 | 0 | 150 | 124/78 | 110/64 | −12 | moderate |
| 4.0 | 0 | 148 | 100/60 | 100/60 | 0 | mild |
| 2.0 | 1.0 | 138 | 120/70 | 126/66 | −4 | moderate |
| 2.0 | 1.0 | 168 | 120/80 | 120/80 | 0 | mild |

TABLE III-continued

| Dosage | | Weight of Patient | Blood Pressure of Patient | | Diastolic Reduction | Complaints of Diuresis |
|---|---|---|---|---|---|---|
| Polythiazide (mg.) | NaCl (gr.) | | Before Ingestion | 9 hours after ingestion of polythiazide | | |
| 2.0 | 1.0 | 135 | 110/70 | 105/60 | −10 | mild |
| 2.0 | 1.0 | 150 | 118/78 | 120/70 | −8 | moderate |
| 2.0 | 1.0 | 148 | 110/60 | 110/60 | 0 | mild |
| 4.0 | 1.0 | 138 | 120/70 | 110/60 | −10 | mild |
| 4.0 | 1.0 | 168 | 120/80 | 120/70 | −10 | mild |
| 4.0 | 1.0 | 135 | 110/60 | 100/60 | 0 | mild |
| 4.0 | 1.0 | 150 | 118/78 | 110/70 | −8 | mild |
| 4.0 | 1.0 | 148 | 118/70 | 110/60 | −10 | severe |

TABLE IIIA

| No. of Patients Tested | Dosage | | Weight Range of Patients (lbs) | Average Blood Pressure of Patients | | Average Diastolic Reduction | Complaints of Diuresis | | |
|---|---|---|---|---|---|---|---|---|---|
| | Polythiazide (mg.) | NaCl (gm.) | | Normal | 9 hours after ingesting polythiazide | | Mild | Moderate | Severe |
| 5 | 2 | 0 | 135–168 | 113.4/70 | 102.8/64 | −6.0 | 1 | 4 | 0 |
| 5 | 4 | 0 | 135–168 | 116.4/69.2 | 104/60.8 | −8.4 | 3 | 1 | 0 |
| 5 | 2 | 1.0 | 135–168 | 115.6/71.6 | 114.2/69.2 | −2.4 | 3 | 2 | 0 |
| 5 | 4 | 1.0 | 135–168 | 117.2/71.6 | 110/68 | −3.6 | 4 | 0 | 1 |

What is claimed:

1. A method for the treatment of acne vulgaris in a human having acne vulgaris which comprises conjointly administering an acne controlling compound induced side effect reducing amount comprising at least 0.2 grams of sodium in a form of a pharmacologically acceptable sodium salt and a therapeutically effective amount of an acne controlling compound selected from the group consisting of polythiazide and trichlormethiazide.

2. A method for the treatment of acne vulgaris in a human having acne vulgaris which comprises conjointly administering on a bi-daily basis an acne controlling compound induced side effect reducing amount comprising at least 0.2 grams of sodium in the form of a pharmacologically acceptable sodium salt and a therapeutically effective amount of an acne controlling compound selected from the group consisting of polythiazide and trichlormethiazide.

3. A pharmacological dose unit which is useful in the treatment of acne vulgaris in a human having acne vulgaris comprising in combination 0.2 grams to 0.8 grams of sodium in the form of a pharmacologically acceptable sodium salt and a therapeutically effective amount of an acne controlling compound selected from the group consisting of polythiazide and trichlormethiazide.

4. A pharmacological dose unit, as defined in claim 3, wherein the acne controlling compound is polythiazide in an amount of 0.5 to 5.0 mg.

5. A pharmacological dose unit, as defined in claim 3, wherein the acne controlling compound is trichlormethiazide in an amount from 0.5 to 5.0 mg.

* * * * *